(12) United States Patent
Mikkaichi et al.

(10) Patent No.: US 8,225,794 B2
(45) Date of Patent: Jul. 24, 2012

(54) OVERTUBE

(75) Inventors: Takayasu Mikkaichi, Tokyo (JP);
Kensei Nakahashi, Tokyo (JP);
Kiyotaka Matsuno, Sagamihara (JP);
Kunihide Kaji, Tokyo (JP)

(73) Assignee: Olympus Medical Systems Corp.,
Tokyo (JP)

( * ) Notice: Subject to any disclaimer, the term of this patent is extended or adjusted under 35 U.S.C. 154(b) by 1267 days.

(21) Appl. No.: 11/331,976

(22) Filed: Jan. 13, 2006

(65) Prior Publication Data

US 2007/0163597 A1 Jul. 19, 2007

(51) Int. Cl.
*A61M 16/00* (2006.01)
*A61M 16/04* (2006.01)

(52) U.S. Cl. ......... 128/207.14; 128/200.26; 128/202.27; 128/204.18; 128/207.15

(58) Field of Classification Search .................. 606/194; 431/226; 128/207.15, 207.14; 604/27
See application file for complete search history.

(56) References Cited

U.S. PATENT DOCUMENTS

| | | | |
|---|---|---|---|
| 5,458,131 A | | 10/1995 | Wilk |
| 5,499,625 A | * | 3/1996 | Frass et al. ............... 128/207.15 |
| 5,660,175 A | * | 8/1997 | Dayal ...................... 128/207.15 |
| 5,827,231 A | * | 10/1998 | Harada .......................... 606/194 |
| 6,790,196 B2 | * | 9/2004 | Kokate et al. .................. 604/28 |
| 6,895,966 B2 | * | 5/2005 | Christopher ............. 128/207.15 |
| 6,939,293 B2 | * | 9/2005 | Conteas ......................... 600/121 |
| 6,961,600 B2 | * | 11/2005 | Kohl et al. ..................... 600/339 |
| RE39,938 E | * | 12/2007 | Brain ....................... 128/207.15 |
| 2007/0089748 A1 | * | 4/2007 | Madsen et al. ........... 128/207.15 |

FOREIGN PATENT DOCUMENTS

| | | |
|---|---|---|
| JP | 63-230162 | 9/1988 |
| JP | 5-9556 | 2/1993 |
| JP | 05-269204 | 10/1993 |
| JP | 07-213614 A | 8/1995 |
| JP | 09-070440 A | 3/1997 |

OTHER PUBLICATIONS

Japanese Office Action dated Feb. 28, 2012 from corresponding Japanese Patent Application No. JP 2008-532255.

* cited by examiner

*Primary Examiner* — Clinton T Ostrup
(74) *Attorney, Agent, or Firm* — Scully, Scott, Murphy & Presser, PC

(57) ABSTRACT

An over-tube of the present invention is an over-tube which guides a device having an insertion section to be inserted into a body of a patient, when inserting the insertion section into or retracting the insertion section from the body of the patient, wherein: a gas-supplying passage is defined between an inner face of the over-tube and the device to be inserted into the over-tube; the gas-supplying passage communicates with a gas-supplying port which is provided on a proximal end side of the over-tube, and a communicating port which is formed on an over-tube insertion section and supplies a gas into a trachea of the patient; and a first sealing member which secures an air passage for communicating the gas-supplying passage and the trachea of the patient via the communicating rod by sealing between a body wall of the patient and the communicating port, is provided on a periphery of an over-tube insertion section.

8 Claims, 7 Drawing Sheets

OVERTUBE

BACKGROUND OF THE INVENTION

1. Field of the Invention

The present invention relates to an over-tube which can supply air to the trachea in addition to acting as a guide for inserting and removing devices such as an endoscope.

2. Description of the Related Art

Laparoscopy is known in which, instead of making a wide incision in the abdominal wall, a plurality of openings are formed in the abdominal wall and performs medical procedures are performed by inserting a hard laparoscope, forceps, and a surgical knife, into each of the openings, in the case in which medical procedures (including an observation, a treatment, or the like.) are performed on internal organs of a human body. Laparoscopy has an advantage in that an early recovery of a patient can be expected since it needs only forming small openings in the abdomen.

However, in recent years, as for medical procedures which further reduce the burden on the patient, performing medical procedures by inserting a flexible endoscope through natural openings such as the mouth, the nose, or the anus, of the patient is proposed. One example of such medical procedures is disclosed in U.S. Pat. No. 5,458,131. This medical procedure will be explained. A flexible endoscope is inserted through the mouth of a patient; and the endoscope is fed into the abdominal cavity through an opening formed in the stomach wall. Observations of the abdominal cavity are performed by an observation device provided on a distal end of the endoscope. Furthermore, treatments of an organ are performed by using: a treatment tool which passes through the endoscope; or a treatment tool which is inserted into the abdominal cavity through another opening formed in the stomach, or which is inserted from the anus into the abdominal cavity through an opening formed in the lower alimentary canal. When the medical procedures within the abdominal cavity are completed, the treatment tool for an endoscope is removed; and the opening is closed. When closing the opening, the organs around the opening are sucked and closed such that the organs are bound together by an O-ring.

SUMMARY OF THE INVENTION

An over-tube according to the present invention is an over-tube which guides a device having an insertion section to be inserted into a body of a patient, when inserting the insertion section into or retracting the insertion section from the body of the patient, wherein: a gas-supplying passage is defined between an inner face of the over-tube and the device to be inserted into the over-tube; the gas-supplying passage communicates with a gas-supplying port which is provided on a proximal end side of the over-tube, and a communicating port which is formed on an over-tube insertion section and supplies a gas into a trachea of the patient; and a first sealing member which secures an air passage for communicating the gas-supplying passage and the trachea of the patient via the communicating port by sealing between a body wall of the patient and the communicating port, is provided on a periphery of an over-tube insertion section.

DETAILED DESCRIPTION OF THE INVENTION

A detailed explanation of embodiments will be made in the following. Moreover, in the following, the same symbols are applied to the same constituent elements. In addition, duplicated explanations will be omitted.

First Embodiment

Figure 1:
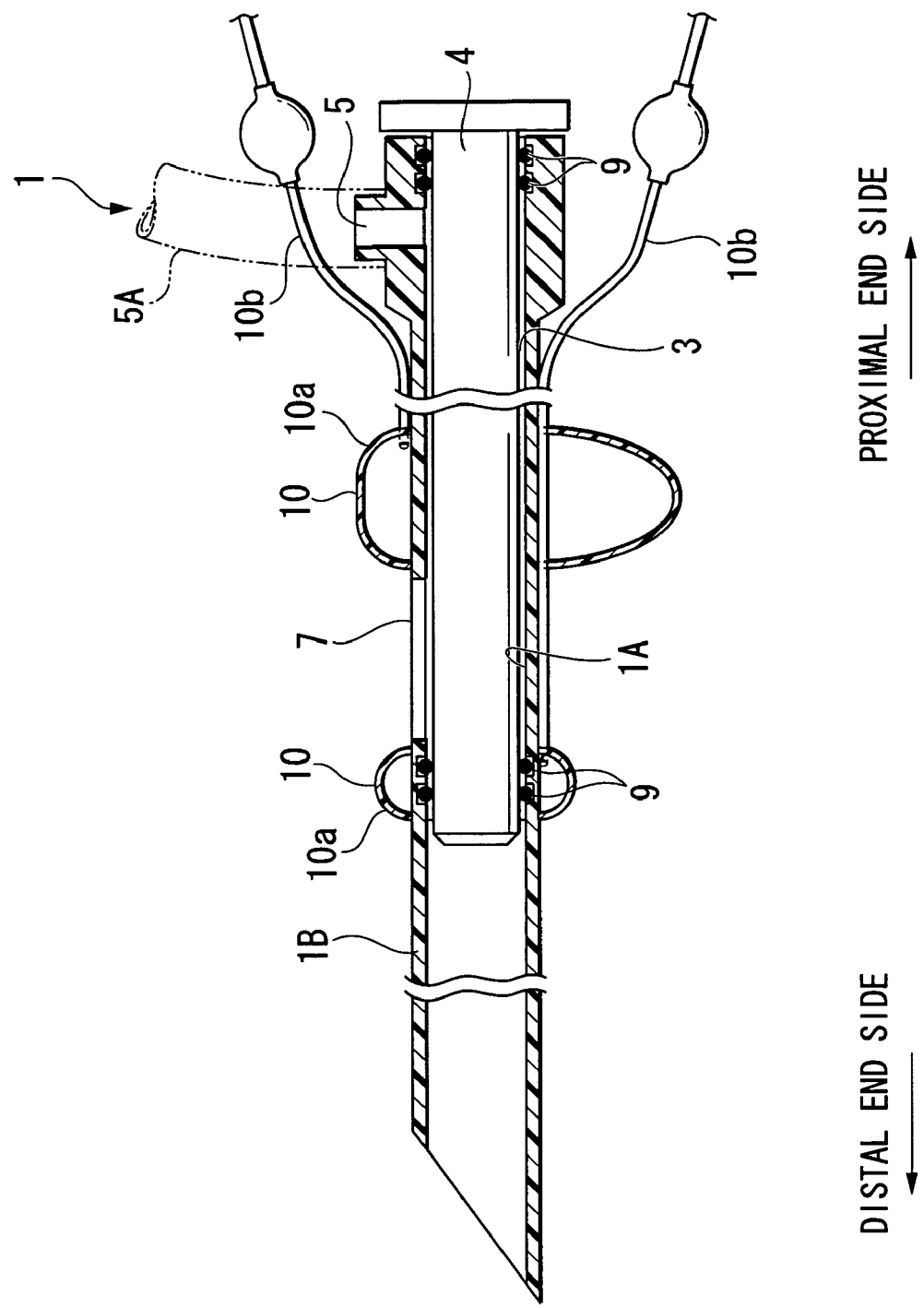
FIG. 1 is a drawing showing an over-tube of a first embodiment of the present invention.

FIG. 1 shows an over-tube of a first embodiment. This over-tube 1 is used by: inserting in advance a distal end side thereof into a body of a patient through the mouth; and guiding a device such as an endoscope 2, having an insertion section to be inserted into the body, when inserting the device into or retracting the device from the body of the patient.

A gas-supplying passage 3 is formed in a ring-shape along the radial direction of the over-tube 1, by a space partitioned by an over-tube inner face 1A and an outer face of a device such as the endoscope 2 to be inserted into the over-tube, or an outer face of a dummy member 4. Moreover, FIG. 1 shows an example in which the dummy member 4 is inserted into the over-tube instead of the device. The dummy member 4 is set to have substantially the same external diameter as that of the device, and is flexible.

The gas-supplying passage 3 communicates with each of a gas-supplying port 5 provided on the over-tube proximal end side, and a communicating port 7 formed on an over-tube insertion section 1B. The over-tube insertion section 1B is a portion on a distal end side of the over-tube 1 (here, the left side of the over-tube 1 in FIG. 1 is denoted as the distal end side while the right side of the over-tube 1 in FIG. 1 is denoted as the proximal end side), and is also a portion to be inserted into the body of the patient.

The gas-supplying port 5 is a portion which is connected to a respirator through a tube 5A, and is formed so as to open on an outer face of the over-tube 1. The communicating port 7 is also formed so as to open on the same side on the outer face of the over-tube 1 as the gas-supplying port 5. The communicating port 7 is formed on a portion facing a larynx 14 of a patient PT (in detail, a portion facing an opening of a trachea 12 (also called the pharynx opening)) when the over-tube 1 is installed into the patient PT.

Sealing members 9 such as O-rings are provided at each of a more distal end side than the communicating portion 7 and a more proximal end side than the gas-supplying port 5, for sealing between an over-tube inner side 1A and the outer face of the device to be inserted into the over-tube.

Moreover, in FIG. 1, two sealing members 9 are provided; however, it is not limited to this, but may be one or more than three.

Sealing members 10 for sealing together with a body wall of the patient PT are attached to each of the proximal end side and the distal end side of the communicating port 7 on the outer face of the over-tube insertion section 1B. For example, cuff balloons 10a are used as the sealing members 10. The cuff balloons 10a expand and contract by receiving a supply of air through cuff tubes 10b.

Next, an operation of the first embodiment will be explained. In the following, explanations for a medical procedure will be made using an example in which: the endoscope 2 is inserted through the mouth of the patient PT; an opening is formed in the stomach wall; and a target region (i.e., internal organs or tissues inside the abdominal cavity) inside the abdominal cavity is treated by approaching into the abdominal cavity. In addition, treatments being medical procedures include an observation, an incision, an inoculation of a cell, a biopsy, a suturing, and the like. For example, medical procedures will be performed, such as an observation of the internal organs inside the abdominal cavity, a biopsy of the liver or the spleen, a cauterization of a myoma of the uterus or the liver (other internal organs), a contraceptive treatment, an extraction of the vermiform appendix or the gallbladder, a bariatric surgery, or the like.

Firstly, the patient PT is anesthetized.

Figure 3:
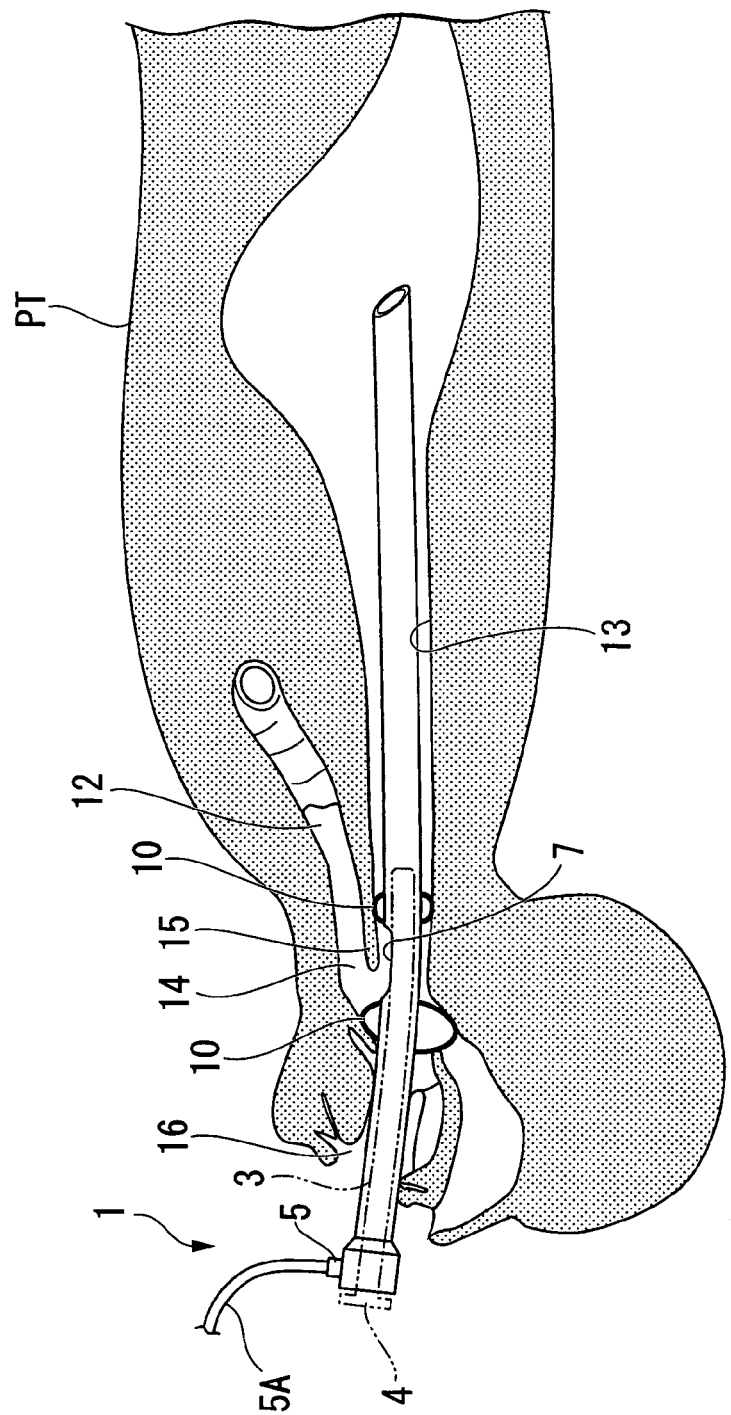
FIG. 3 is an explanatory drawing when the over-tube is installed into a patient.

Next, as shown in FIG. 3, the head of the patient PT is directed downwards and is fixed such that each of the trachea 12 and an esophagus 13 becomes substantially straight. By this, a passage from the pharynx region to a musculus arytenoideus transversus 15, through which the over-tube 1 passes can be substantially linear.

Figure 2:
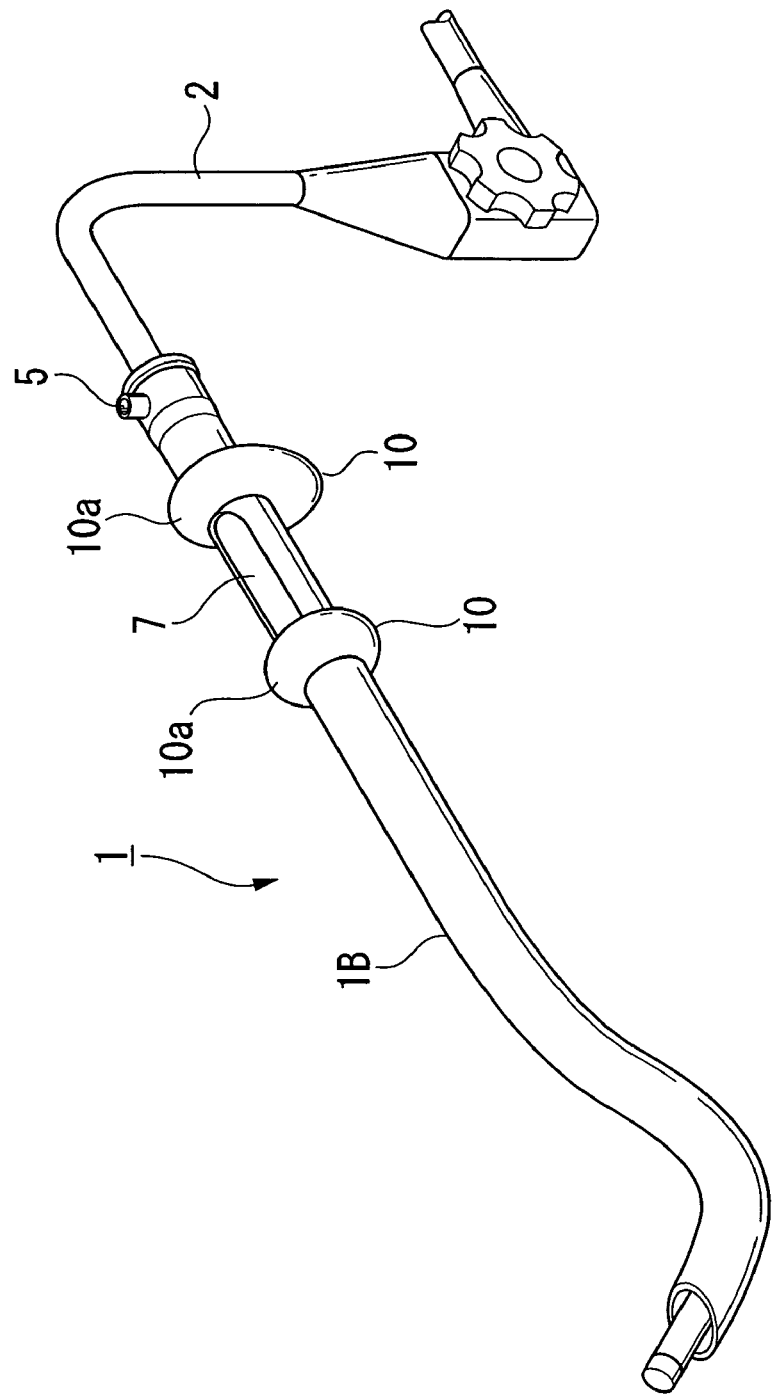
FIG. 2 is a drawing showing a status in which an endoscope is inserted into the over-tube.

Next, as shown in FIG. 2, the endoscope 2 is inserted into the over-tube 1, and the over-tube 1 is inserted into the body of the patient PT through a mouth 16 together with the endoscope 2.

Insertion of the over-tube 1 is stopped at the time when the communicating port 7 reaches a position facing the larynx 14. At this time, the distal end of the over-tube 1 reaches the esophagus 10 or the stomach. Then, air is supplied to the cuff balloons 10a through the cuff tubes 10b, and thereby expanding the cuff balloons 10a. By this, an air passage for communicating the gas-supplying passage 3 of the over-tube 1 and the trachea 12 of the patient PT is secured.

Next, the gas-supplying port 5 of the over-tube 1 is connected to the respirator though the tube 5A; thereby, supplying necessary air, oxidant gas, or anesthesia gas into the lungs of the patient PT through the gas-supplying passage 3 inside the over-tube 1, and artificially controlling the breathing of the patient PT.

In addition, at this time, since the gas-supplying passage 3 is formed in a ring-shape along the radial direction of the over-tube 1, a large cross-sectional area can be secured; thereby, the resistance for supplying gas can be made as small as possible.

Furthermore, gas is supplied to the patient PT using the gas-supplying passage 3 formed between the inner face of the over-tube and the outer face of the endoscope 2. Accordingly, burden on the pharynx region of the patient PT can be reduced compared with supplying gas using a trachea tube which is provided in addition to the over-tube 1, since the diameter of the over-tube 1 having a function of supplying gas and a function of guiding the device can be made as small as possible.

Moreover, in the case in which the over-tube and the trachea tube are used together, the over-tube and the trachea tube are overlapped with each other in the pharynx region of the patient PT, and the width-dimension of an overlapped portion will be extremely large. Thus, burden on the pharynx region of the patient PT will be extremely large.

At this time, the breathing of and anesthesia for the patient are controlled. Moreover, in the case in which the endoscope 2 is removed, the dummy member 4 will be inserted instead. The one reason for inserting the dummy member 4 into the over-tube 1 is to secure the gas-supplying passage 3 in the over-tube 1.

Moreover, when removing the devices such as the endoscope from the over-tube 1 or inserting the devices into the over-tube 1, since the gas-supplying port 5 is formed on the outer face of the over-tube 1, a possibility of causing interference between the gas-supplying port 5 or the tubes 5A to be connected thereto and the endoscope 2 to be removed or the dummy member 4 to be inserted, is small; thereby, insertion and retraction operations of the endoscope 2 or the like can be made easily.

In the case in which a treatment is started, the dummy member 4 is removed and the endoscope 2 is inserted. When the distal end of the endoscope reaches the stomach, gas is supplied into the stomach using a channel within the endoscope; thereby, expanding the stomach. Then, the stomach wall is incised by a high-frequency knife inserted in a channel within the endoscope.

Subsequently, a pneumoperitoneum needle is embedded in the abdomen of the patient PT, and carbonic acid gas or the like is supplied into the abdominal cavity; thereby, expanding the abdominal cavity. The reason for expanding the abdominal cavity is to secure a space for performing medical procedures in the abdominal cavity. As for a method for expanding the abdominal cavity, carbonic acid gas may be supplied into the abdominal cavity using a channel within the endoscope instead of using the pneumoperitoneum needle.

Moreover, the diaphragm of the patient PT is pressed while in the pneumoperitoneum condition. Especially, in the case in which the amount of anesthesia is large, natural breath becomes hard; therefore, breathing-control will be performed. In the present embodiment, breathing of the patient is artificially controlled using the gas-supplying passage 3 secured inside the over-tube 1.

Subsequently, an opening is formed in a front wall of the stomach while replacing the endoscope 2 in accordance with necessity. Then, an approach to the target region existing inside the abdominal cavity is made while making the insertion section of the endoscope 2 proceed into the abdominal cavity through the formed opening portion; and thereafter, a desired treatment is performed on the target region.

Moreover, the reason for replacing the endoscope 2 in accordance with necessity is: that the required cleanliness is different between the inside of the stomach and the inside of the abdominal cavity; and that the most suitable device for the treatment at that time needs to be used.

When replacing the endoscope 2 like this, there was a concern about applying a severe burden on the narrow pharynx region of the patient PT; however, also in this case, as mentioned in the above, gas is supplied to the patient using the gas-supplying passage 3 secured inside the over-tube, and the diameter of the over-tube having a function of supplying gas and a function of guiding the devices can be as small as possible; therefore, burden on the pharynx region of the patient PT can be small.

Furthermore, like this, since breathing control is performed using the over-tube 1, in accordance with necessity, it is also possible to switch, during the operation, from a medical procedure using the endoscope to a conventional medical procedure in which the abdominal wall is widely incised.

When the necessary treatment inside the abdominal cavity is completed, the distal end of the endoscope is retracted to the inside of the stomach; and the opening portion is sutured by a treatment tool for suture which is attached to the endoscope or is inserted in a working channel within the endoscope (i.e., a connection between the inside of the lumen internal organs and the abdominal cavity is closed).

Subsequently, the endoscope 2 is removed from the patient PT and the dummy member 4 is inserted instead. The over-tube 1 is left until the breathing control of the patient becomes unnecessary. Then, when the breathing control becomes unnecessary, the over-tube 1 is removed from the patient PT. Otherwise, after completing treatment inside the body of the patient, the endoscope 2 and the over-tube 1 are removed from the body; and thereafter, a trachea tube may be inserted instead until the breathing control becomes unnecessary.

Figure 4:
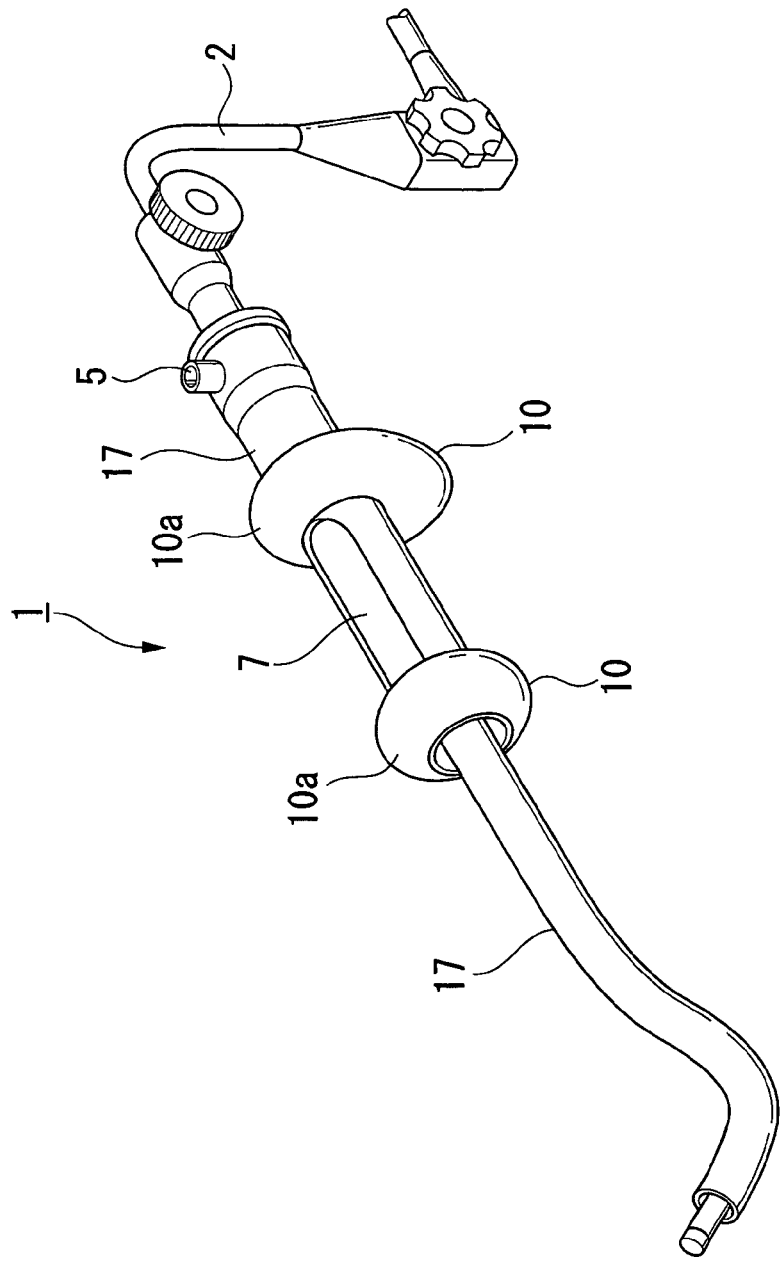
FIG. 4 is a drawing showing a status in which a sub over-tube and the endoscope are inserted into the over-tube.

Moreover, in the first embodiment, the endoscope 2 is directly inserted into the over-tube 1; however, it is not limited to this configuration, and as shown in FIG. 4, it may be arranged such that: a sub over-tube 17 is firstly inserted into the over-tube 1 having a shorter length; and the endoscope 2 is inserted into the inside of the sub over-tube 17 while using it. Furthermore, treatment devices such as forceps, a high-frequency knife, or the like may be inserted instead of the endoscope 2. The important point is forming the gas-supplying passage between the over-tube 1 and the devices inserted therein.

Second Embodiment

Figure 5:
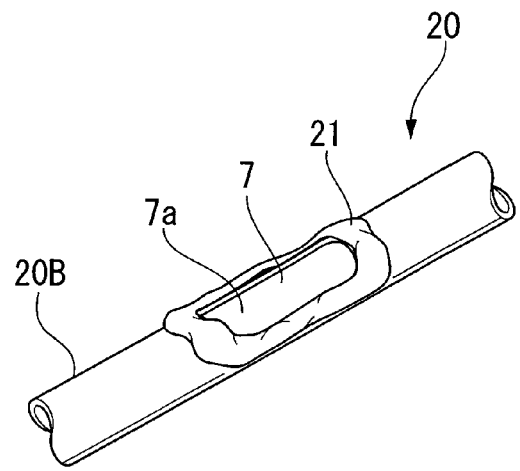
FIG. 5 is a drawing showing one part of an over-tube of a second embodiment of the present invention.

FIG. 5 shows an over-tube of a second embodiment. As with the above-mentioned first embodiment, this over-tube 20 is also used by installing it into the patient through the mouth. The special feature of this over-tube 20 is that a sealing member 21 which covers around an opening 7a of the communicating port 7 and seals together with the body wall of the patient, is provided on an outer portion of an over-tube insertion section 20B. The sealing member 21 is entirely in the shape of a ring-shaped bag, and receives a supply of air through an air tube 22.

Figure 6:
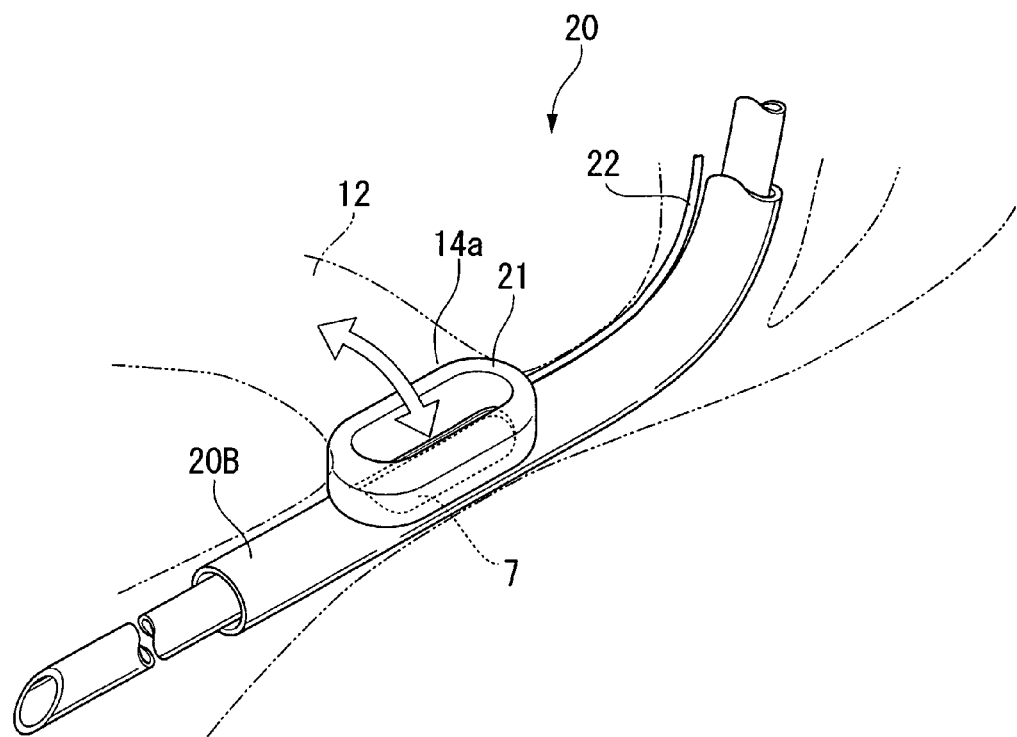
FIG. 6 is an explanatory drawing for the over-tube in an operating condition.

According to this over-tube 20, after installing it at a normal position inside the body of the patient, if air is supplied to the sealing member 21 through the air tube, then the sealing member 21 will expand as shown in FIG. 6, and will adhere to the body wall near a laryngeal inlet 14a of the patient. By this, an air passage communicating between the communicating port 7 and the trachea 12 can be secured. Furthermore, this over-tube 20 also can decrease burden on the pharynx region of the patient while maintaining the necessary amount of supply gas.

Third Embodiment

Figure 7:
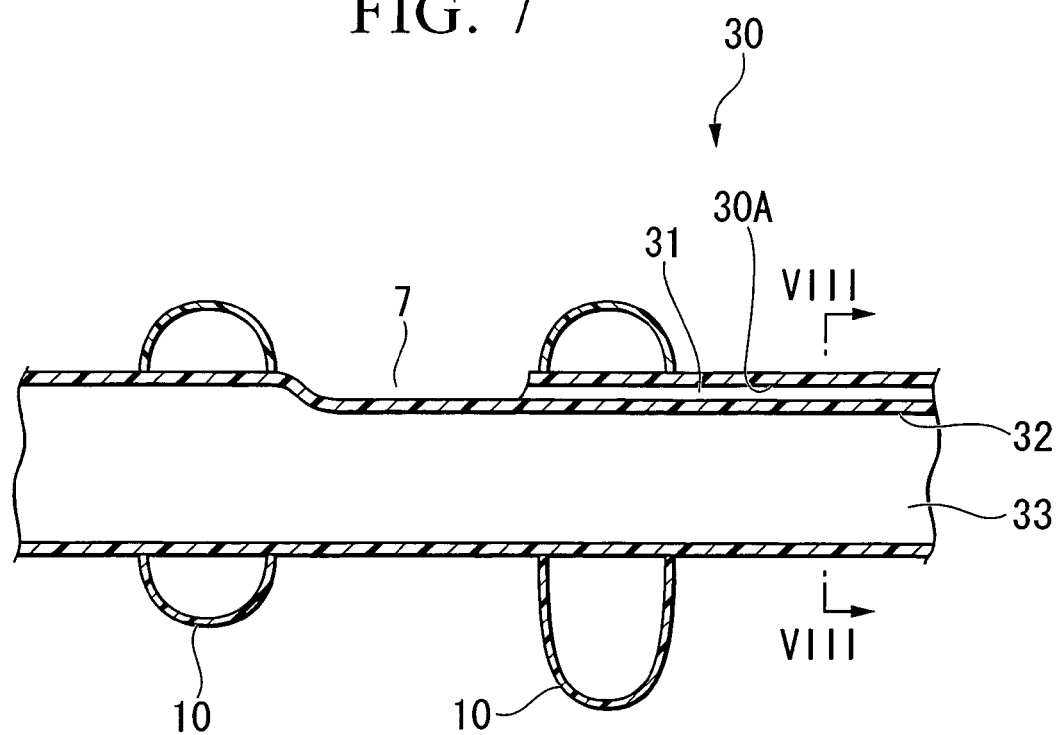
FIG. 7 is a cross-sectional drawing of one part of an over-tube of a third embodiment of the present invention.

FIG. 7 shows an over-tube of a third embodiment. This over-tube 30 is used by being installed into the patient through the mouth. The special feature of this over-tube 30 is that a gas-supplying passage 31 thereinside is formed by a space partitioned by an over-tube inner face 30A and a partitioning member 32 provided inside the over-tube. The partitioning member 32 is formed in a plate-shape, and is formed so as to extend from a more proximal end side than the gas-supplying port 5 to a more distal end side than the communicating port 7.

According to the over-tube 30 of the present embodiment, an inside thereof is divided by the partitioning member 32 into the gas-supplying passage 31 and a space 33 for inserting devices. Thus, since the diameter of the over-tube 30 having a function of supplying gas and a function of guiding the devices can be as small as possible, burden on the pharynx region of the patient when inserting and retracting the devices can be small while maintaining the necessary amount of supply gas for the breathing of the patient.

In addition, according to the over-tube 30 of the present invention, there is an advantage in that the gas-supplying passage can be secured all the time without inserting the devices or the dummy member therein, since the gas-supplying passage 31 is secured only by the tube itself.

Figure 8:
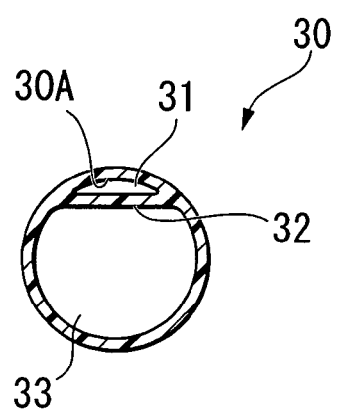
FIG. 8 is a cross-sectional drawing taken along a line VIII-VIII of FIG. 7.

Moreover, FIGS. 7 and 8 show a case in which the partitioning member 32 is formed in a single piece together with a tube body; however, it is not limited to this configuration, and it may be provided separately with respect to the tube body.

Fourth Embodiment

Figure 9:
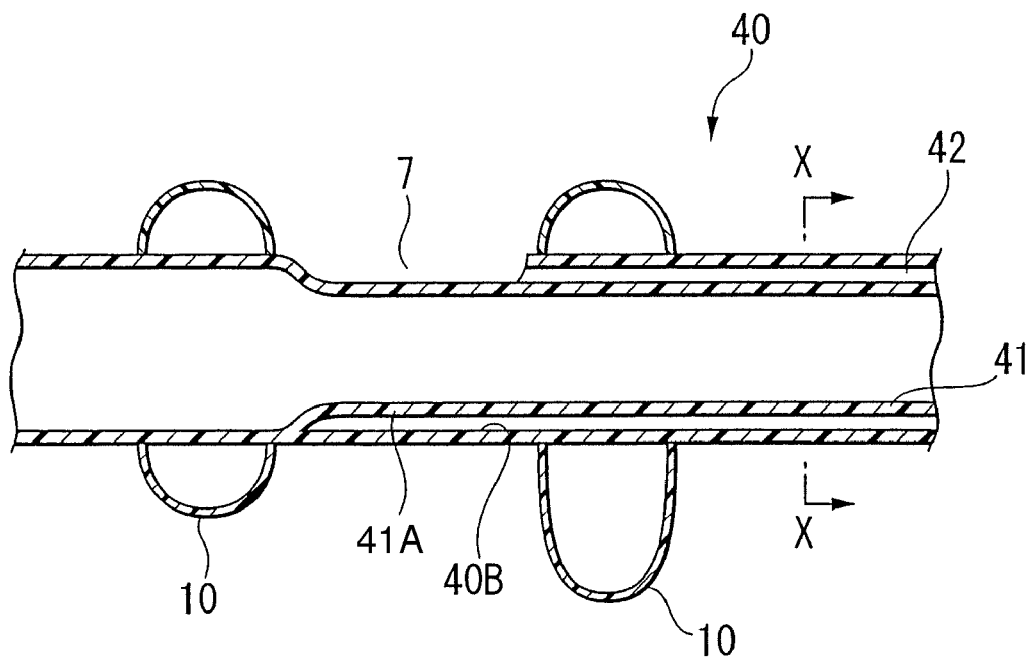
FIG. 9 is a cross-sectional drawing of one part of an over-tube of a fourth embodiment of the present invention.
Figure 10:
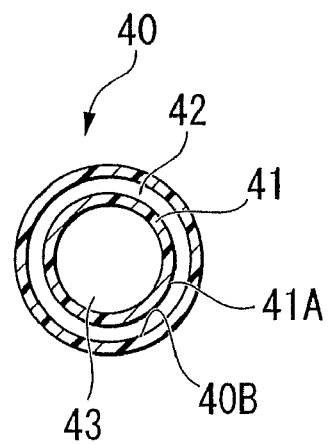
FIG. 10 is a cross-sectional drawing taken along a line X-X of FIG. 9.

FIG. 9 shows an over-tube of a fourth embodiment. This over-tube 40 is used by being installed into the patient through the mouth. The special feature of this over-tube 40 is that: a partitioning member provided thereinside is formed by a tube-shaped member 41; and a gas-supplying passage 42 is formed to have a cross-section of a ring-shape by an outer face 41A of the tube-shaped member 41 and an over-tube inner face 40B. The tube-shaped member 41 is formed so as to extend from a more proximal end side than the gas-supplying port 5 to a more distal end side than the communicating port 7.

According to this over-tube 40, the inside thereof is divided by the tube-shaped member 41 into the gas-supplying passage 42 on the outer side and a space 43 for inserting devices on the inner side. Thus, since the diameter of the over-tube 1 having a function of supplying gas and a function of guiding the devices can be as small as possible, burden on the pharynx region of the patient when inserting and retracting the devices can be small while maintaining the necessary amount of supply gas for the breathing of the patient. Furthermore, according to the over-tube 40 of the present embodiment, since the gas-supplying passage 42 is formed in a ring shape, a large cross-sectional area can be secured; therefore, it is suitable for the case in which it is necessary to secure a larger amount of supply gas.

Moreover, in the over-tube 40 of the present embodiment, ribs may be provided in accordance with necessity between the ring-shaped member 41 and the tube on the outside thereof, in order to secure an adequate gap therebetween.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An over-tube which guides a device having an insertion section to be inserted into a body of a patient, when inserting the insertion section into or retracting the insertion section from the body of the patient, the over-tube comprising:
a distal tip opening configured to be capable of the device being protruded therefrom;
a gas-supplying port which is provided on a circumference of a proximal end side of the over-tube; and
a communicating port which is formed on a circumference of an insertion section of the over-tube, is positioned at a more proximal end side than the distal tip opening and a more distal end side than the gas-supplying port, and supplies a gas into a trachea of the patient, second sealing members provided with the over-tube at each of a more distal end side than the communicating portion and a more proximal end side than the gas-supplying port, and fixed with respect to the over-tube wherein the over-tube is configured to be capable of forming a gas-supplying passage between an inner face of the over-tube and the insertion section of the device when the device is inserted into the over-tube;

the second sealing members are configured to be capable of sealing the gas-supplying passage between an over-tube inner face and the outer face of the device when the device is inserted into the over-tube;

the gas-supplying passage communicates with the gas-supplying port and the communicating port;

a gas from the gas-supplying port is supplied into the trachea of the patient while passing through the gas-supplying passage and the communicating port; and a first sealing member which secures an air passage for communicating the gas-supplying passage and the trachea of the patient via the communicating port by sealing between a body wall of the patient and the communicating port, is provided on an outer face of the over-tube.

2. The over-tube of claim 1, wherein the communicating port, is formed so as to open on the same side of the outer face on the over-tube as the gas-supplying port.

3. The over-tube according to claim 2, wherein: a partitioning member is formed by a tube-shaped member; and the gas-supplying passage is formed so as to have a ring-shaped cross section by an outer face of the tube-shaped member and the inner face of the over-tube.

4. The over-tube according to claim 2, wherein the first sealing member includes a first section positioned at a more distal end side than the communicating port and a second section positioned at a more proximal end side than the communicating port.

5. The over-tube according to claim 1, further comprising a dummy member which is inserted into the over-tube so as to be capable of being pulled out, while the device is not inserted, and defines the gas-supplying passage together with the inner face of the over-tube.

6. The over-tube according to claim 1, wherein:

the communicating port has an opening on the circumference of the over-tube insertion section; and the first sealing member includes at least a pair of sealing portions formed on the circumference of the over-tube along a radial direction of the over-tube insertion section, so as to sandwich the opening therebetween.

7. The over-tube according to claim 1, wherein:

the communicating port has an opening on the circumference of the over-tube insertion section; and the first sealing member includes a sealing portion formed on the circumference of the over-tube so as to surround the opening.

8. The over-tube according to claim 1, wherein the first sealing member includes a first section positioned at a more distal end side than the communicating port and a second section positioned at a more proximal end side than the communicating port.

* * * * *